United States Patent
Bulliard et al.

(10) Patent No.: US 9,960,362 B2
(45) Date of Patent: May 1, 2018

(54) COMPOUND AND ORGANIC PHOTOELECTRIC DEVICE, IMAGE SENSOR AND ELECTRONIC DEVICE INCLUDING THE SAME

(71) Applicant: Samsung Electronics Co., Ltd., Suwon-si, Gyeonggi-do (KR)

(72) Inventors: Xavier Bulliard, Seongnam-si (KR); Tadao Yagi, Hwaseong-si (KR); Rie Sakurai, Suwon-si (KR); Hiromasa Shibuya, Seongnam-si (KR); Kwang Hee Lee, Yongin-si (KR); Dong-Seok Leem, Hwaseong-si (KR); Hyesung Choi, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days. days.

(21) Appl. No.: 15/609,125

(22) Filed: May 31, 2017

(65) Prior Publication Data
US 2017/0346016 A1 Nov. 30, 2017

(30) Foreign Application Priority Data
May 31, 2016 (KR) .................. 10-2016-0067401

(51) Int. Cl.
| | |
|---|---|
| *C07D 307/66* | (2006.01) |
| *H01L 51/00* | (2006.01) |
| *H01L 51/44* | (2006.01) |
| *H01L 27/30* | (2006.01) |
| *C07D 405/06* | (2006.01) |

(52) U.S. Cl.
CPC ........ *H01L 51/0061* (2013.01); *C07D 307/66* (2013.01); *C07D 405/06* (2013.01); *H01L 27/307* (2013.01); *H01L 51/006* (2013.01); *H01L 51/441* (2013.01); *H01L 51/447* (2013.01); *H01L 51/0046* (2013.01); *H01L 51/0053* (2013.01); *H01L 51/0065* (2013.01); *H01L 51/0067* (2013.01)

(58) Field of Classification Search
CPC . H01L 51/0061; H01L 27/307; H01L 51/006; H01L 51/441; H01L 51/447; H01L 51/0046; H01L 51/0053; H01L 51/0065; H01L 51/0067; C07D 405/06
See application file for complete search history.

(56) References Cited

U.S. PATENT DOCUMENTS

| | | | |
|---|---|---|---|
| 8,525,577 B2 | 9/2013 | Yofu et al. | |
| 2016/0111651 A1* | 4/2016 | Yun ..................... | H01L 51/4253 257/40 |
| 2017/0294589 A1* | 10/2017 | Shibuya .............. | H01L 51/0067 |

* cited by examiner

*Primary Examiner* — Alexander R Pagano
(74) *Attorney, Agent, or Firm* — Harness, Dickey & Pierce, P.L.C.

(57) ABSTRACT

A compound is represented by Chemical Formula 1, and an organic photoelectric device, an image sensor, and an electronic device include the compound.

[Chemical Formula 1]

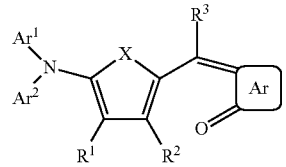

In Chemical Formula 1, each substituent is the same as defined in the detailed description.

22 Claims, 7 Drawing Sheets

COMPOUND AND ORGANIC PHOTOELECTRIC DEVICE, IMAGE SENSOR AND ELECTRONIC DEVICE INCLUDING THE SAME

CROSS-REFERENCE TO RELATED APPLICATION

This application claims priority to Korean Patent Application No. 10-2016-0067401 filed in the Korean Intellectual Property Office on May 31, 2016, and all the benefits accruing therefrom under 35 U.S.C. § 119, the content of which is incorporated herein in its entirety by reference.

BACKGROUND

1. Field

Example embodiments relate to a compound and an organic photoelectric device, an image sensor, and an electronic device including the same.

2. Description of Related Art

A photoelectric device may convert light into an electrical signal using photoelectric effects. A photoelectric device may include a photodiode, a phototransistor, etc. A photoelectric device may be applied to an image sensor, a solar cell, an organic light emitting diode, etc.

An image sensor including a photodiode requires relatively high resolution and thus a smaller pixel. At present, a silicon photodiode is widely used. In some cases, a silicon photodiode exhibits a problem of deteriorated sensitivity because of a relatively small absorption area due to relatively small pixels. Accordingly, an organic material that is capable of replacing silicon has been researched.

An organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide a compound that selectively absorbs light in a green wavelength region.

Example embodiments also provide an organic photoelectric device capable of selectively absorbing light in a green wavelength region and improving efficiency.

Example embodiments also provide an image sensor including the organic photoelectric device.

Example embodiments also provide an electronic device including the image sensor.

According to example embodiments, a compound represented by Chemical Formula 1 is provided.

[Chemical Formula 1]

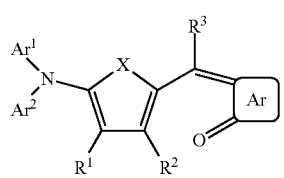

In Chemical Formula 1, Ar may be one of a substituted or unsubstituted 5-membered aromatic ring, a substituted or unsubstituted 6-membered aromatic ring, and a combination thereof in a condensed ring. X may be one of O and $NR^a$ (wherein $R^a$ may be one of hydrogen and a substituted or unsubstituted C1 to C10 alkyl group). Each of $Ar^1$ and $Ar^2$ independently may be one of a substituted or unsubstituted C6 to C30 aryl group and a substituted or unsubstituted C3 to C30 heteroaryl group. Each of $R^1$, $R^2$, and $R^3$ independently may be one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof.

In some example embodiments, each of $Ar^1$ and $Ar^2$ independently may be one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

In some example embodiments, in Chemical Formula 1, a ring group represented by Ar bound to a methine group may be represented by Chemical Formula 2.

[Chemical Formula 2]

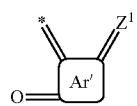

In Chemical Formula 2, Ar' may be one of a substituted or unsubstituted 5-membered aromatic ring, a substituted or unsubstituted 6-membered aromatic ring, and a combination thereof in a condensed ring. Also, $Z^1$ may be one of O and $CR^bR^c$, wherein $R^b$ and $R^c$ independently may be one of hydrogen, a substituted or unsubstituted C1 to C10 alkyl group, a cyano group, or a cyano-containing group, provided that at least one of $R^b$ and $R^c$ is a cyano group or a cyano-containing group.

In some example embodiments, in Chemical Formula 1, a ring group represented by Ar bound to a methine group may be represented by one of Chemical Formulae 3-1 to 3-4.

[Chemical Formula 3-1]

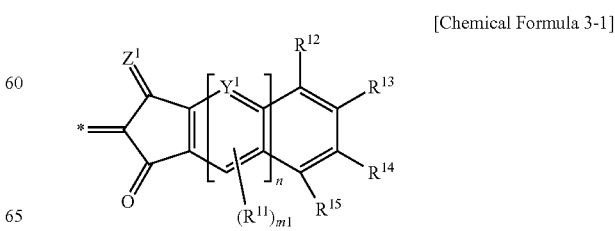

In Chemical Formula 3-1, $Z^1$ may be one of O and $CR^bR^c$ (wherein $R^b$ and $R^c$ independently may be one of hydrogen, a substituted or unsubstituted C1 to C10 alkyl group, a cyano group, or a cyano-containing group, provided that at least one of $R^b$ and $R^c$ may be a cyano group and a cyano-containing group), $Y^1$ may be one of N and $CR^d$ (wherein $R^d$ is one of hydrogen and a substituted or unsubstituted C1 to C10 alkyl group); each of $R^1$, $R^{12}$, $R^{13}$, $R^{14}$, and $R^{15}$ may be independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, or $R^{12}$ and $R^{13}$ and $R^{14}$ and $R^{15}$ may be independently linked with each other to form an aromatic ring; m1 may be 0 or 1; and n may be 0 or 1.

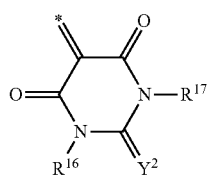

[Chemical Formula 3-2]

In Chemical Formula 3-2, $Y^2$ may be one of O, S, Se, Te, and $C(R^e)(CN)$ (wherein $R^e$ may be one of hydrogen, a cyano group (—CN), and a C1 to C10 alkyl group); each of $R^{16}$ and $R^{17}$ independently may be one of hydrogen, a substituted or unsubstituted C1 to C30 alkyl group, a substituted or unsubstituted C6 to C30 aryl group, a substituted or unsubstituted C4 to C30 heteroaryl group, halogen, a cyano group (—CN), and a combination thereof.

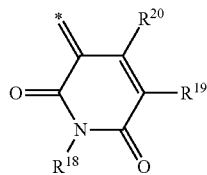

[Chemical Formula 3-3]

In Chemical Formula 3-3, each of $R^{18}$ to $R^{20}$ independently may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof.

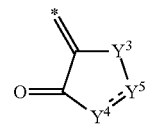

[Chemical Formula 3-4]

In Chemical Formula 3-4, $Y^3$ may be one of O, S, Se, and Te; $Y^4$ may be one of N and $NR^f$; $Y^5$ may be one of $CR^g$ and $C=(CR^h)(CN)$; and each of $R^f$, $R^g$, and $R^h$ independently may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof.

In some example embodiments, the compound may be represented by one of Chemical Formulae 4-1 to 4-4.

[Chemical Formula 4-1]

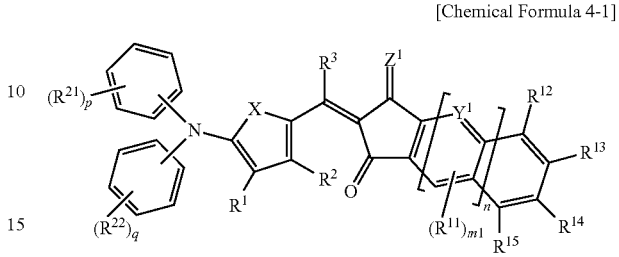

In Chemical Formula 4-1, X may be one of O and $NR^a$ (wherein $R^a$ may be one of hydrogen and a substituted or unsubstituted C1 to C10 alkyl group); $Z^1$ may be one of O and $CR^bR^c$ (wherein $R^b$ and $R^c$ independently may be one of hydrogen, a substituted or unsubstituted C1 to C10 alkyl group, a cyano group, and a cyano-containing group, provided that at least one of $R^b$ and $R^c$ is a cyano group or a cyano-containing group); $Y^1$ may be one of N and $CR^d$ (wherein $R^d$ may be one of hydrogen and a substituted or unsubstituted C1 to C10 alkyl group); each of $R^1$, $R^{12}$, $R^{13}$, $R^{14}$, and $R^{15}$ independently may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, or $R^{12}$ and $R^{13}$ and $R^{14}$ and $R^{15}$ may be independently linked with each other to form an aromatic ring; m1 may be one of 0 and 1; n may be one of 0 or 1; each of $R^{21}$ and $R^{22}$ independently may be one of hydrogen, a halogen, a cyano group (—CN), a cyano-containing group, a substituted or unsubstituted C1 to C6 alkyl group, a substituted or unsubstituted C1 to C6 alkoxy group, and a combination thereof; p may be an integer ranging from 0 to 3; and q may be an integer ranging from 0 to 4.

[Chemical Formula 4-2]

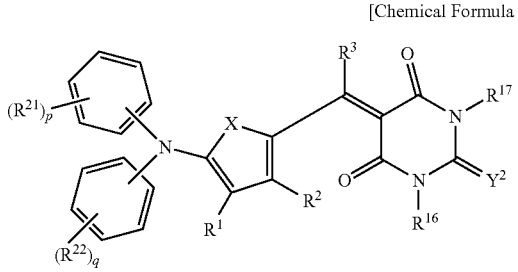

In Chemical Formula 4-2, X may be one of O and $NR^a$ (wherein $R^a$ may be one of hydrogen and a substituted or unsubstituted C1 to C10 alkyl group); $Y^2$ may be one of O, S, Se, Te, and $C(R^e)(CN)$ (wherein $R^e$ is one of hydrogen, a cyano group (—CN), and a C1 to C10 alkyl group); each of $R^1$, $R^2$, $R^3$, $R^{16}$, and $R^{17}$ independently may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof; each of $R^{21}$ and $R^{22}$ independently may be one of hydrogen, a halogen, a cyano group (—CN), a cyano-containing group, a substituted or unsubstituted C1 to C6 alkyl group, a substituted or unsubstituted C1 to C6 alkoxy group, and a combination thereof; p may be an integer ranging from 0 to 3; and q may be an integer ranging from 0 to 4.

[Chemical Formula 4-3]

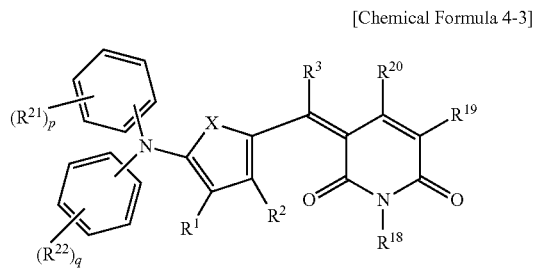

In Chemical Formula 4-3, X may be one of O and $NR^a$ (wherein $R^a$ may be one of hydrogen and a substituted or unsubstituted C1 to C10 alkyl group); each of $R^{21}$ and $R^{22}$ independently may be one of hydrogen, a halogen, a cyano group (—CN), a cyano-containing group, a substituted or unsubstituted C1 to C6 alkyl group, a substituted or unsubstituted C1 to C6 alkoxy group, and a combination thereof; each of $R^1$, $R^2$, $R^3$, $R^{18}$, $R^{19}$, and $R^{20}$ independently may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof; each of $R^{21}$ and $R^{22}$ independently may be one of hydrogen, a halogen, a cyano group (—CN), a cyano-containing group, a substituted or unsubstituted C1 to C6 alkyl group, a substituted or unsubstituted C1 to C6 alkoxy group, and a combination thereof; p may be an integer ranging from 0 to 3; and q may be an integer ranging from 0 to 4.

[Chemical Formula 4-4]

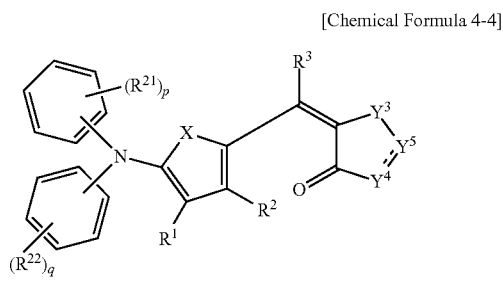

In Chemical Formula 4-4, X may be one of O and $NR^a$ (wherein $R^a$ is one of hydrogen and a substituted or unsubstituted C1 to C10 alkyl group); $Y^3$ may be one of O, S, Se, and Te; $Y^4$ may be one of N and $NR^f$; $Y^5$ may be one of $CR^g$ and $C=(CR^h)(CN)$; $R^1$, $R^2$, $R^3$, $R^f$, $R^g$, and $R^h$ independently may be one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof; and $R^{21}$ and $R^{22}$ independently may be one of hydrogen, a halogen, a cyano group (—CN), a cyano-containing group, a substituted or unsubstituted C1 to C6 alkyl group, a substituted or unsubstituted C1 to C6 alkoxy group, and a combination thereof; p may be an integer ranging from 0 to 3; and q may be an integer ranging from 0 to 4.

In some example embodiments, the compound may selectively absorbs light in a green wavelength region and may have a maximum absorption wavelength ($\lambda_{max}$) in a wavelength region of about 500 nm to about 600 nm, for example about 520 nm to about 560 nm in a thin film state.

In some example embodiments, compound may exhibit a light absorption curve having a full width at half maximum (FWHM) of about 50 nm to about 120 nm, in a thin film state.

According to some example embodiments, an organic photoelectric device includes a first electrode and a second electrode facing each other and an active layer interposed between the first electrode and the second electrode and including the compound represented by Chemical Formula 1.

In some example embodiments, at least one of $Ar^1$ and $Ar^2$ in Chemical Formula 1 independently may one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

In some example embodiments, the compound in the active layer may be represented by one of Chemical Formulae 4-1 to 4-4.

In some example embodiments, the active layer may have a maximum absorption wavelength ($\lambda_{max}$) in a wavelength region of about 500 nm to about 600 nm, for example about 520 nm to about 560 nm.

In some example embodiments, the active layer may exhibit a light absorption curve having a full width at half maximum (FWHM) of about 50 nm to about 120 nm.

In some example embodiments, the active layer may have an absorption coefficient of greater than or equal to about $5.0 \times 10^4$ when including the compound and C60 in a volume ratio of about 0.9:1 to about 1.1:1.

According to some example embodiments, an image sensor may include the organic photoelectric device.

In some example embodiments, the image sensor may include a semiconductor substrate integrated with a plurality of first photo-sensing devices sensing light in a blue wavelength region and a plurality of second photo-sensing devices sensing light in a red wavelength region, and the organic photoelectric device on the semiconductor substrate and selectively sensing light in a green wavelength region.

In some example embodiments, the first photo-sensing device and the second photo-sensing device may be stacked in a vertical direction in the semiconductor substrate.

In some example embodiments, the image sensor may further include a color filter layer between the semiconductor substrate and the organic photoelectric device, and including a blue filter selectively absorbing light in a blue wavelength region and a red filter selectively absorbing light in a red wavelength region.

In some example embodiments, the image sensor may include a green photoelectric device of the organic photoelectric device, a blue photoelectric device selectively absorbing light in a blue wavelength region, and a red photoelectric device selectively absorbing light in a red wavelength region that are stacked.

According to some example embodiments, an electronic device may include the image sensor.

DETAILED DESCRIPTION

Figure 1:
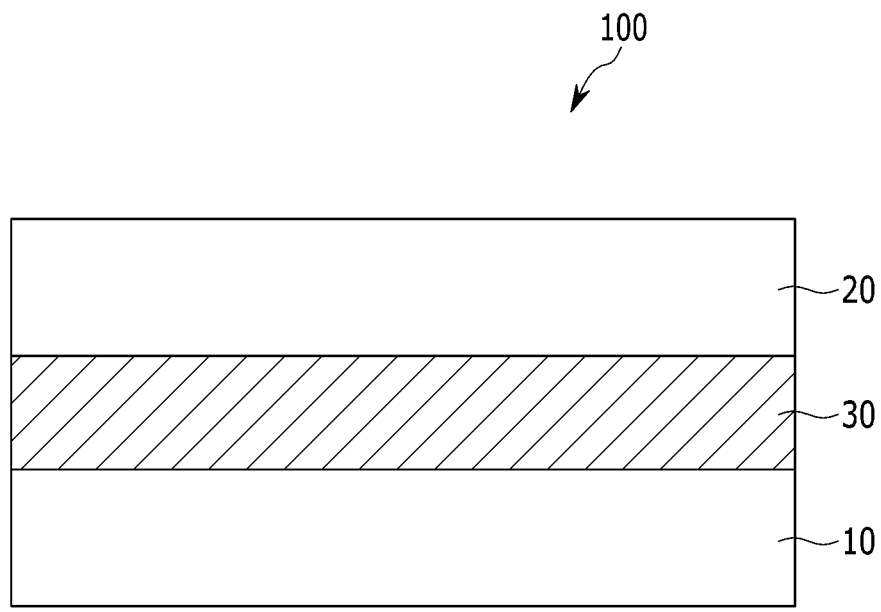
FIG. 1 is a cross-sectional view showing an organic photoelectric device according to an embodiment.

Example embodiments will hereinafter be described in detail, and may be easily performed by those who have common knowledge in the related art. However, this disclosure may be embodied in many different forms and is not to be construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numerals throughout the specification.

As used herein, when specific definition is not otherwise provided, the term "substituted" refers to one substituted with a substituent selected from a halogen atom (F, Cl, Br, or I), a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C1 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof, instead of hydrogen of a compound.

As used herein, when specific definition is not otherwise provided, the term "hetero" refers to one including 1 to 3 heteroatoms selected from N, O, S, P, and Si.

As used herein, the term "alkyl group" for example refers to a methyl group, an ethyl group, a propyl group, an isopropyl group, a n-butyl group, an isobutyl group, a t-butyl group, a pentyl group, a hexyl group, and the like.

As used herein, the term "cycloalkyl group" for example refers to a cyclopropyl group, a cyclobutyl group, a cyclopentyl group, a cyclohexyl group, and the like.

As used herein, the term "aryl group" refers to a substituent including all element of the cycle having p-orbitals which form conjugation, and may be a monocyclic, polycyclic or fused ring polycyclic (i.e., rings sharing adjacent pairs of carbon atoms) functional group.

As used herein, when a definition is not otherwise provided, the term "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as a dicyanoalkenyl group represented by $=CR^{x'}-(CR^{x}R^{y})_{p}-CR^{y'}(CN)_{2}$ wherein $R^{x}$, $R^{y}$, $R^{x'}$, and $R^{y'}$ are independently hydrogen or a C1 to C10 alkyl group and p is an integer of 0 to 10. Specific examples of the cyano-containing group may be a dicyanomethyl group, a dicyanovinyl group, a cyanoethynyl group, and the like As used herein, when a definition is not otherwise provided, the term "combination thereof" refers to at least two substituents bound to each other by a single bond or a C1 to C10 alkylene group, or at least two fused substituents.

As used herein, the term "5-membered aromatic ring" refers to a 5-membered cyclic group (e.g., C5 aryl group) having a conjugation structure or a 5-membered heterocyclic group (e.g., C2 to C4 heteroaryl group) having a conjugation structure. As used herein, the term "6-membered aromatic ring" refers to a 6-membered cyclic group (e.g., C6 aryl group) having a conjugation structure or a 6-membered heterocyclic group (e.g., C2 to C5 heteroaryl group) having a conjugation structure.

As used herein, the term "aromatic ring" refers to a substituted or unsubstituted C6 to C30 aryl group, for example a substituted or unsubstituted C6 to C20 aryl group or a substituted or unsubstituted C4 to C30 heteroaryl group, for example a substituted or unsubstituted C4 to C20 heteroaryl group.

Hereinafter, a compound according to an embodiment is described.

A compound according to an embodiment is represented by Chemical Formula 1.

[Chemical Formula 1]

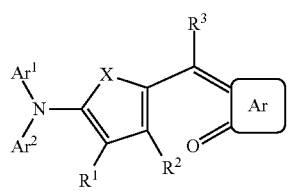

In Chemical Formula 1,

Ar is one of a substituted or unsubstituted 5-membered aromatic ring, a substituted or unsubstituted 6-membered aromatic ring, and a condensed ring of two or more of the foregoing rings, X is one of O and $NR^a$ (wherein $R^a$ is one of hydrogen and a substituted or unsubstituted C1 to C10 alkyl group), each of $Ar^1$ and $Ar^2$ are independently one of a substituted or unsubstituted C6 to C30 aryl group and a substituted or unsubstituted C3 to C30 heteroaryl group, and each of $R^1$, $R^2$, and $R^3$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof.

In an embodiment, in $Ar^1$, $Ar^2$, Ar, and $R^1$ to $R^3$, "substituted" for example refers to substitution with a halogen (F, Cl, Br, or I), a cyano group (—CN), a C1 to C6 alkyl group or a C1 to C6 alkoxy group, but is not limited thereto. In another embodiment, the halogen may be a chloro group (—Cl) or a fluoro group (—F).

In Chemical Formula 1, each of $R^1$ to $R^3$ may be for example independently selected from hydrogen, a substituted or unsubstituted C1 to C10 alkyl group, a substituted or unsubstituted C6 to C12 aryl group, a substituted or unsubstituted C3 to C10 heteroaryl group, a halogen, a cyano group (—CN), a cyano-containing group, and a combination thereof.

The number of the aromatic rings of the compound may range from 4 to 7, for example 5 to 7. When the number of the aromatic ring ranges from 4 to 7, a selective absorption property in a green wavelength region is improved. Herein "aromatic ring" refers to a substituted or unsubstituted 5-membered or 6-membered ring that provides a conjugation structure.

Each of $Ar^1$ and $Ar^2$ may be a substituted or unsubstituted C6 to C30 aryl group or a substituted or unsubstituted C3 to C30 heteroaryl group aromatic rings are present alone or fused together, for example a substituted or unsubstituted C6 to C20 aryl group or a substituted or unsubstituted C3 to C20 heteroaryl group aromatic rings are present alone or fused together. In other words, a conjugation structure of the aromatic groups connected through a single bond between the aromatic rings or another linking group is broken, failing in providing a sufficient conjugation length.

Each of $Ar^1$ and $Ar^2$ may independently be selected from a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

In example embodiments, each of $Ar^1$ and $Ar^2$ may be the same or different.

The compound represented by Chemical Formula 1 includes an electron donor moiety of arylamine and an electron acceptor moiety represented by Ar.

In Chemical Formula 1, the ring group represented by Ar bound to a methine group is an electron acceptor moiety including at least one carbonyl group.

For example, in Chemical Formula 1, the ring group represented by Ar bound to a methine group may include one carbonyl group or two carbonyl groups.

For example, in Chemical Formula 1, the ring group represented by Ar bound to a methine group may include at least one carbonyl group and at least one cyano-containing moiety.

In Chemical Formula 1, the ring group represented by Ar bound to a methine group may be for example represented by Chemical Formula 2.

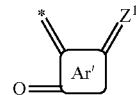

[Chemical Formula 2]

In Chemical Formula 2,

Ar' is one of a substituted or unsubstituted 5-membered aromatic ring, a substituted or unsubstituted 6-membered aromatic ring, and a condensed ring of two or more of the foregoing rings, and $Z^1$ is O or $CR^bR^c$, wherein $R^b$ and $R^c$ are independently hydrogen, a substituted or unsubstituted C1 to C10 alkyl group, a cyano group, or a cyano-containing group, provided that at least one of $R^b$ and $R^c$ is a cyano group or a cyano-containing group.

For example, in Chemical Formula 1, the ring group represented by Ar bound to a methine group may be a condensed ring of a substituted or unsubstituted 5-membered aromatic ring and a substituted or unsubstituted 6-membered aromatic ring.

In Chemical Formula 1, the ring group represented by Ar bound to a methine group may be for example a ring group represented by one of Chemical Formulae 3-1 to 3-4.

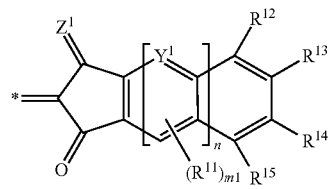

[Chemical Formula 3-1]

In Chemical Formula 3-1, $Z^1$ is O or $CR^bR^c$ (wherein $R^b$ and $R^c$ are independently hydrogen, a substituted or unsubstituted C1 to C10 alkyl group, a cyano group, or a cyano-containing group, provided that at least one of $R^b$ and $R^c$ is a cyano group or a cyano-containing group), $Y^1$ is one of N and $CR^d$ (wherein $R^d$ is one of hydrogen and a substituted or unsubstituted C1 to C10 alkyl group), $R^{11}$, $R^{12}$, $R^{13}$, $R^{14}$, and $R^{15}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof or $R^{12}$ and $R^{13}$ and $R^{14}$ and $R^{15}$ are independently linked with each other to form an aromatic ring, m1 is 0 or 1, and n is 0 or 1.

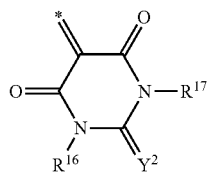

[Chemical Formula 3-2]

In Chemical Formula 3-2, $Y^2$ is one of O, S, Se, Te, and $C(R^e)(CN)$ (wherein $R^e$ is one of hydrogen, a cyano group (—CN), and a C1 to C10 alkyl group), and each of $R^{16}$ and $R^{17}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), and a combination thereof.

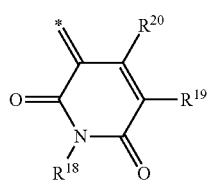

[Chemical Formula 3-3]

In Chemical Formula 3-3, each of $R^{18}$ to $R^{20}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof.

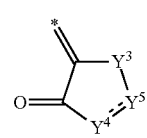

[Chemical Formula 3-4]

In Chemical Formula 3-4, $Y^3$ is one of O, S, Se, and Te, $Y^4$ is N or $NR^f$, $Y^5$ is $CR^g$ or $C=(CR^h)(CN)$, and each of $R^f$, $R^g$, and $R^h$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof.

The ring group represented by Chemical Formula 3-1 may be for example a ring group represented by one of Chemical Formulae 3-1-1, 3-1-2 or 3-1-3.

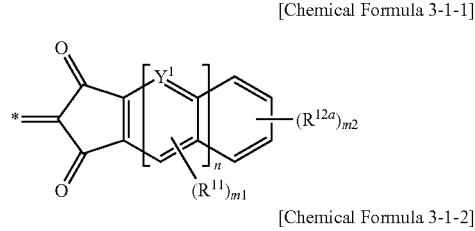

[Chemical Formula 3-1-1]

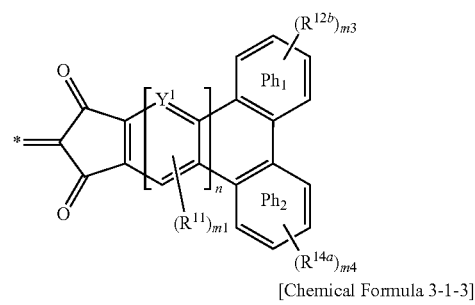

[Chemical Formula 3-1-2]

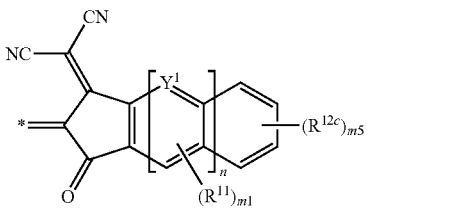

[Chemical Formula 3-1-3]

In Chemical Formulae 3-1-1, 3-1-2, and 3-1-3, $Y^1$, $R^{11}$, n, m1, and m2 are the same as in Chemical Formula 3-1, each of $R^{12a}$, $R^{12b}$, $R^{12c}$, and $R^{14a}$ may independently be selected from hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, m2, m3, m4, and m5 are independently an integer ranging from 0 to 4 (and/or 1 to 4), Ph1 and Ph2 are a fused phenylene ring and one of Ph1 and Ph2 may optionally be omitted.

The ring group represented by Chemical Formula 3-3 may be for example a ring group represented by Chemical Formula 3-3-1 or 3-3-2.

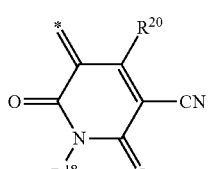

[Chemical Formula 3-3-1]

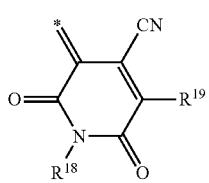

[Chemical Formula 3-3-2]

In Chemical Formulae 3-3-1 and 3-3-2, $R^{18}$, $R^{19}$, and $R^{20}$ are the same as described above in Chemical Formula 3-3.

The ring group represented by Chemical Formula 3-4 may be for example a ring group represented by Chemical Formula 3-4-1 or 3-4-2.

[Chemical Formula 3-4-1]

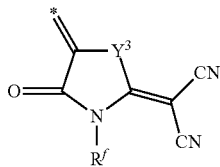

[Chemical Formula 3-4-2]

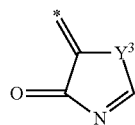

In Chemical Formulae 3-4-1 and 3-4-2, $Y^3$ and $R^f$ are same as described in Chemical Formula 3-4.

The compound may be a compound represented by one of Chemical Formulae 4-1 to 4-4.

[Chemical Formula 4-1]

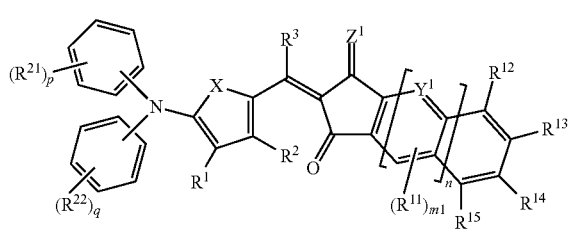

In Chemical Formula 4-1,

X is one of O and $NR^a$ (wherein $R^a$ is one of hydrogen and a substituted or unsubstituted C1 to C10 alkyl group), $Z^1$ is O or $CR^bR^c$ (wherein $R^b$ and $R^c$ are independently hydrogen, a substituted or unsubstituted C1 to C10 alkyl group, a cyano group, or a cyano-containing group, provided that at least one of $R^b$ and $R^c$ is a cyano group or a cyano-containing group), $Y^1$ is one of N and $CR^d$ (wherein $R^d$ is one of hydrogen and a substituted or unsubstituted C1 to C10 alkyl group), each of $R^{11}$, $R^{12}$, $R^{13}$, $R^{14}$, and $R^{15}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof or $R^{12}$ and $R^{13}$ and $R^{14}$ and $R^{15}$ are independently linked with each other to form an aromatic ring, m1 is 0 or 1, n is 0 or 1, each of $R^{21}$ and $R^{22}$ are independently one of hydrogen, a halogen, a cyano group (—CN), a cyano-containing group, a substituted or unsubstituted C1 to C6 alkyl group, a substituted or unsubstituted C1 to C6 alkoxy group, and a combination thereof, p is an integer ranging from 0 to 3 (and/or 1 to 3), and q is an integer ranging from 0 to 4 (and/or 1 to 4).

[Chemical Formula 4-2]

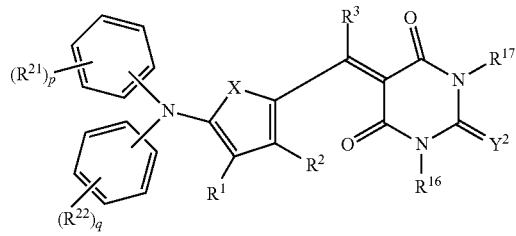

In Chemical Formula 4-2,

X is one of O and $NR^a$ (wherein $R^a$ is one of hydrogen and a substituted or unsubstituted C1 to C10 alkyl group), $Y^2$ is one of O, S, Se, Te, and $C(R^e)(CN)$ (wherein $R^e$ is one of hydrogen, a cyano group (—CN), and a C1 to C10 alkyl group), each of $R^1$, $R^2$, $R^3$, $R^{16}$, and $R^{17}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, each of $R^{21}$ and $R^{22}$ are independently one of hydrogen, a halogen, a cyano group (—CN), a cyano-containing group, a substituted or unsubstituted C1 to C6 alkyl group, a substituted or unsubstituted C1 to C6 alkoxy group, and a combination thereof, p is an integer ranging from 0 to 3 (and/or 1 to 3), and q is an integer ranging from 0 to 4 (and/or 1 to 4).

[Chemical Formula 4-3]

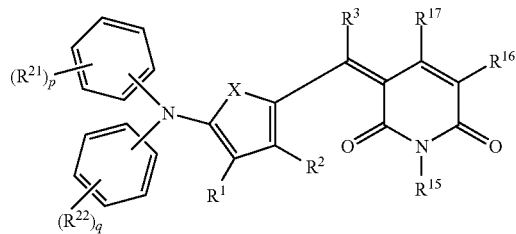

In Chemical Formula 4-3,

X is one of O and $NR^a$ (wherein $R^a$ is one of hydrogen and a substituted or unsubstituted C1 to C10 alkyl group), and each of $R^1$, $R^2$, $R^3$, $R^{18}$, $R^{19}$, and $R^{20}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof.

[Chemical Formula 4-4]

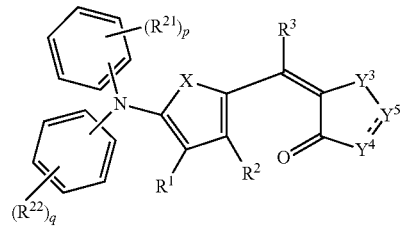

In Chemical Formula 4-4,

X is one of O and NR$^a$ (wherein R$^a$ is one of hydrogen and a substituted or unsubstituted C1 to C10 alkyl group), Y$^3$ is one of O, S, Se, and Te, Y$^4$ is N or NR$^f$, Y$^5$ is CR$^g$ or C=(CR$^h$)(CN), each of R$^1$, R$^2$, R$^3$, R$^f$, R$^g$, and R$^h$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, each of R$^{21}$ and R$^{22}$ are independently one of hydrogen, a halogen, a cyano group (—CN), a cyano-containing group, a substituted or unsubstituted C1 to C6 alkyl group, a substituted or unsubstituted C1 to C6 alkoxy group, and a combination thereof, p is an integer ranging from 0 to 3 (and/or 1 to 3), and q is an integer ranging from 0 to 4 (and/or 1 to 4).

Examples of the compound of Chemical Formula 1 may be compounds of Chemical Formula 5-1, but are not limited thereto.

[Chemical Formula 5-1]

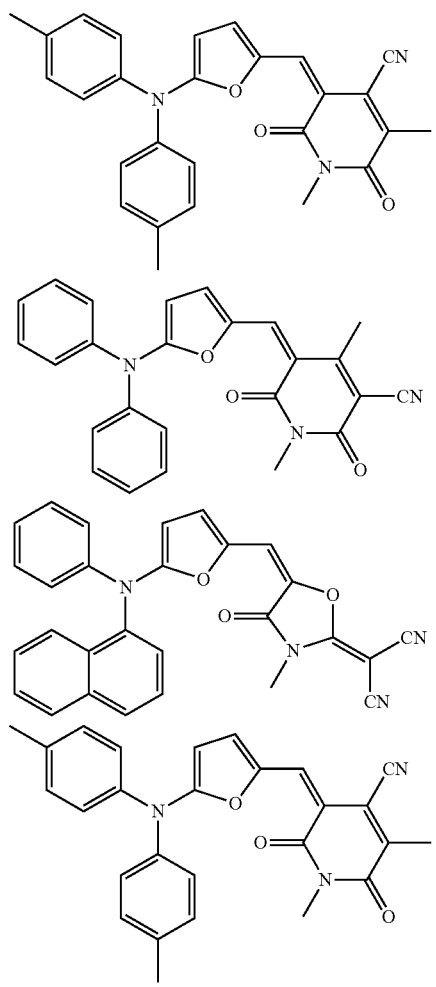

-continued

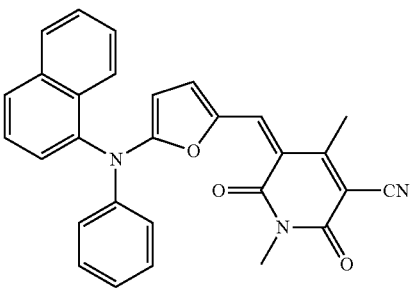

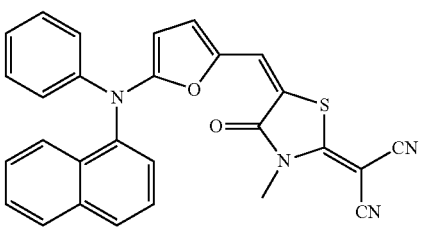

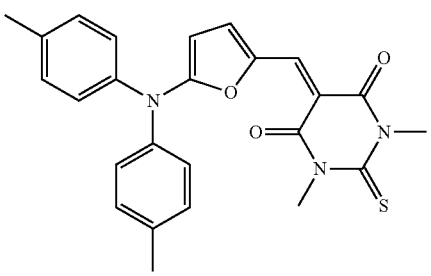

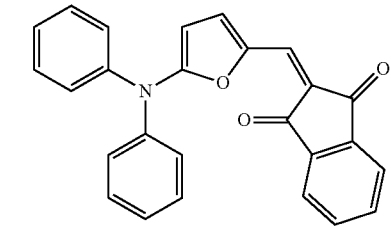

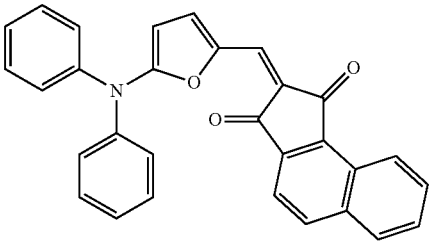

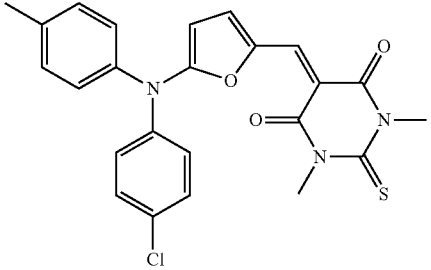

-continued
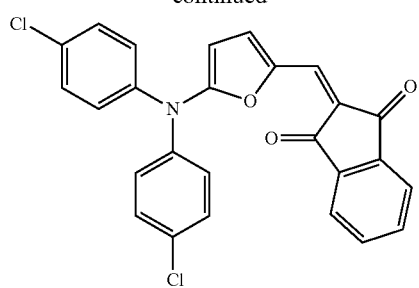
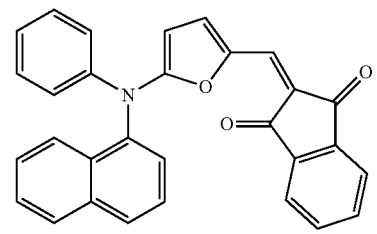
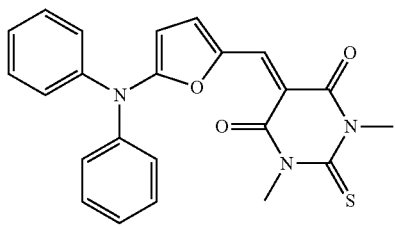
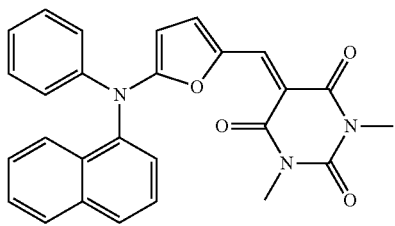
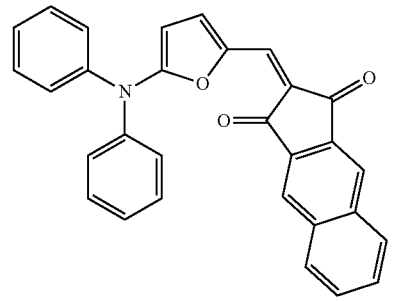
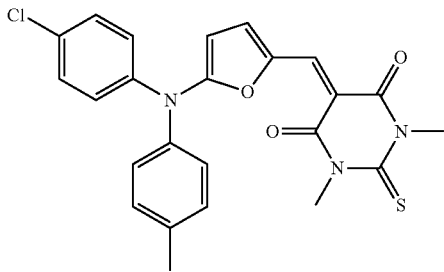
-continued
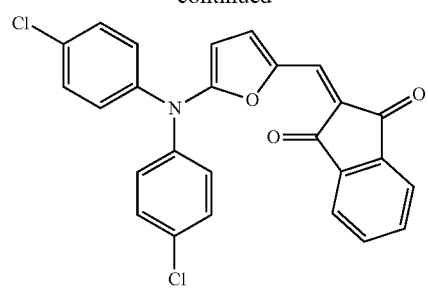
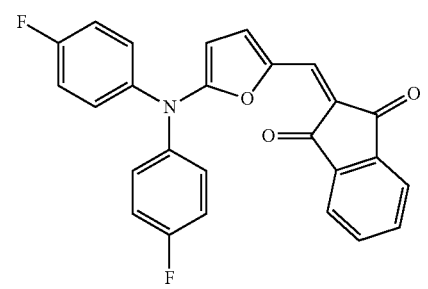
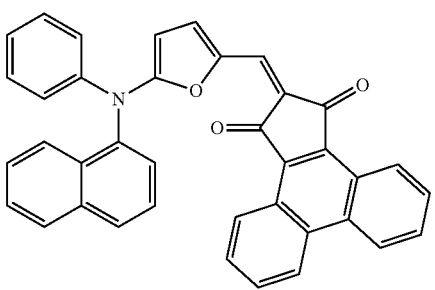
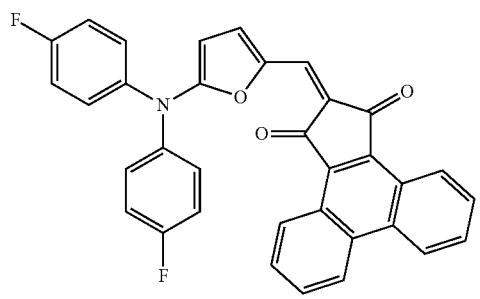
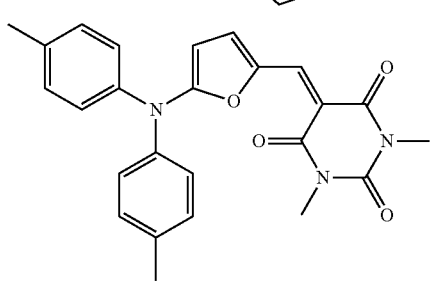

-continued

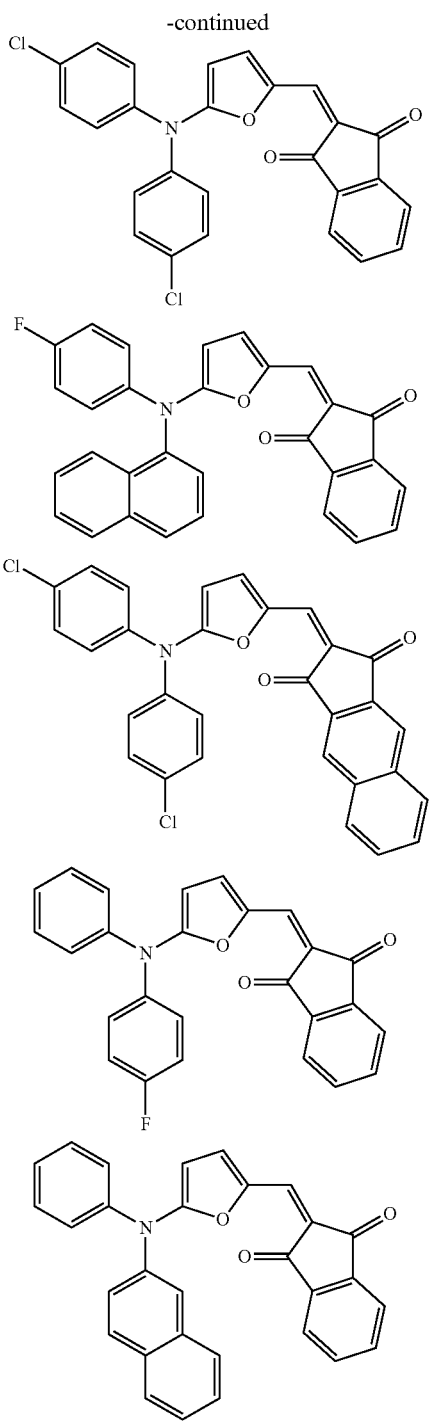

The compound is a compound that selectively absorbs light in a green wavelength region, and may have a maximum absorption wavelength ($\lambda_{max}$) in a wavelength region of about 500 nm to about 600 nm, for example about 520 nm to about 560 nm in a thin film state.

The active layer may have an absorption coefficient of greater than or equal to about $5.0 \times 10^4$, for example greater than or equal to about $6.0 \times 10^4$ cm$^{-1}$, about $6.0 \times 10^4$ to about $10 \times 10^4$ cm$^{-1}$ or about $7.0 \times 10^4$ cm$^{-1}$ to about $10 \times 10^4$ cm$^{-1}$ when including the compound and C60 in a volume ratio of about 0.9:1 to about 1.1:1, for example 1:1.

The compound may exhibit a light absorption curve having a full width at half maximum (FWHM) of about 50 nm to about 120 nm, in a thin film state.

Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may have thermal decomposition temperature ($T_d$) of greater than or equal to about 280° C. The compound may have for example a thermal decomposition temperature ($T_d$) of about 280° C. to about 500° C., for example about 285° C. to about 450° C. The thermal decomposition temperature ($T_d$) is a temperature at which a compound starts to be decomposed and thus, does not maintain its intrinsic molecular structure but is transformed. In general, atoms in a molecule consisting of a compound are volatilized and lost into the air or vacuum at greater than or equal to a thermal decomposition temperature, and thus, the thermal decomposition temperature may be regarded as a temperature at which initial weight of the compound starts to be decreased by heat.

Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the appropriate HOMO-LUMO level of the compound, when the compound has a HOMO level ranging from about 5.0 eV to about 5.8 eV and an energy bandgap ranging from about 1.9 eV to about 2.3 eV, the LUMO level of the compound is in a range of about 3.9 eV to about 2.7 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

The compound may have a molecular weight of about 300 to about 1,500, specifically about 350 to about 1,200, and more specifically about 400 to about 900. When the compound has a molecular weight within the range, the crystallinity of the first compound and thermal decomposition during formation of a thin film by deposition may be inhibited.

The compound may have a melting point of greater than or equal to about 200° C., more specifically greater than or equal to about 250° C., and still more specifically greater than or equal to about 280° C. When the compound has a melting point within this range (e.g., at least 200° C.), a thin film may be stably deposited and an amount decomposed product is decreased, and thus an organic photoelectric device having improved photoelectric conversion performance is provided.

The compound may be a p-type semiconductor compound.

Hereinafter, an organic photoelectric device including the compound is described.

FIG. 1 is a cross-sectional view showing an organic photoelectric device according to an example embodiment.

Referring to FIG. 1, an organic photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength ($\lambda_{max}$) in a wavelength region of about 500 nm to about 600 nm, specifically about 515 nm to about 570 nm, and more specifically about 520 nm to about 560 nm.

The active layer 30 may exhibit a light absorption curve having a relatively narrow full width at half maximum (FWHM) of about 50 nm to about 110 nm, for example about 50 nm to about 100 nm. Accordingly, the active layer 30 has high selectivity for light in a green wavelength region.

The active layer 30 may further include an n-type semiconductor compound for forming a pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent attached thereto. The fullerene derivative may include a substituent such as alkyl group, aryl group, or a heterocyclic group. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

The sub-phthalocyanine or the sub-phthalocyanine derivative may be represented by Chemical Formula 6.

[Chemical Formula 6]

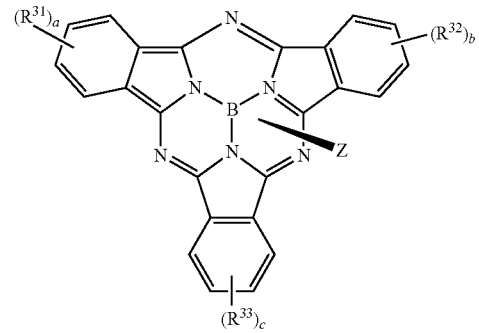

In Chemical Formula 6,
each of $R^{31}$ to $R^{33}$ are independently one of hydrogen, a substituted or unsubstituted C1 to C30 alkyl group, a substituted or unsubstituted C6 to C30 aryl group, a substituted or unsubstituted C3 to C30 heteroaryl group, halogen, a halogen-containing group, and a combination thereof,
a, b, and c are an integer ranging from 1 to 3, and
Z is a monovalent substituent.

For example, Z may be a halogen or a halogen-containing group, for example F, Cl, a F-containing group, or a Cl-containing group.

The halogen may refer to F, Cl, Br, or I, and the halogen-containing group may refer to an alkyl group where at least one of hydrogen is replaced by F, Cl, Br, or I.

The thiophene derivative may be for example represented by Chemical Formula 7 or Chemical Formula 8, but is not limited thereto.

[Chemical Formula 7]

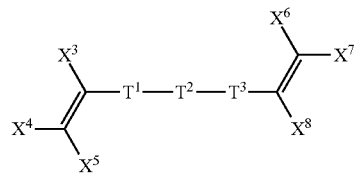

[Chemical Formula 8]

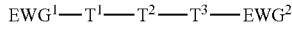

In Chemical Formulae 7 and 8,
each of $T^1$, $T^2$, and $T^3$ are aromatic rings including substituted or unsubstituted thiophene moieties,
each of $T^1$, $T^2$, and $T^3$ are independently present or are fused to each other,
each of $X^3$ to $X^8$ are independently hydrogen, a substituted or unsubstituted C1 to C30 alkyl group, a substituted or unsubstituted C6 to C30 aryl group, a substituted or unsubstituted C3 to C30 heterocyclic group, a cyano group, or a combination thereof, and
each of $EWG^1$ and $EWG^2$ are independently an electron withdrawing group.

For example, in Chemical Formula 7, at least one of $X^3$ to $X^8$ is an electron withdrawing group, for example a cyano group or a cyano-containing group.

The active layer 30 may further include a second p-type semiconductor compound selectively absorbing green light. The p-type semiconductor compound may be a compound represented by Chemical Formula 9.

[Chemical Formula 9]

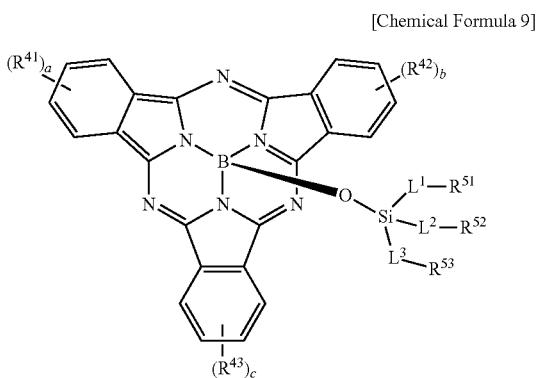

In Chemical Formula 9, each of $R^{41}$ to $R^{43}$ are independently one of hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, a thiol group, a substituted or unsubstituted C6 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or adjacent two groups of $R^{41}$ to $R^{43}$ are optionally fused to each other to provide a ring, each of $L^1$ to $L^3$ are independently one of a single bond, a substituted or unsubstituted C1 to C30 alkylene group, a substituted or unsubstituted C6 to C30 arylene group, divalent substituted or unsubstituted C3 to C30 heterocyclic group, and a combination thereof, each of $R^{51}$ to $R^{53}$ are independently one of a substituted or unsubstituted C1 to C30 alkyl group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, and a combination thereof, and a to c are independently an integer ranging from 0 to 4 (and/or 1 to 4).

The second p-type semiconductor compound selectively absorb green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced and a pn junction may be effectively formed.

The p-type layer may include the semiconductor compound of Chemical Formula 1 and the n-type layer may include the n-type semiconductor compound.

The active layer 30 may have a thickness of about 1 nm to about 500 nm, and specifically, about 5 nm to about 300 nm. When the active layer 30 has a thickness within the range, the active layer may effectively absorb light, effectively separate holes from electrons, and deliver them, thereby effectively improving photoelectric conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90%.

In the organic photoelectric device 100, when light enters from the first electrode 10 and/or second electrode 20, and when the active layer 30 absorbs light having a desired (and/or alternatively predetermined) wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectric device.

Hereinafter, an organic photoelectric device according to another embodiment is described with reference to FIG. 2.

Figure 2:
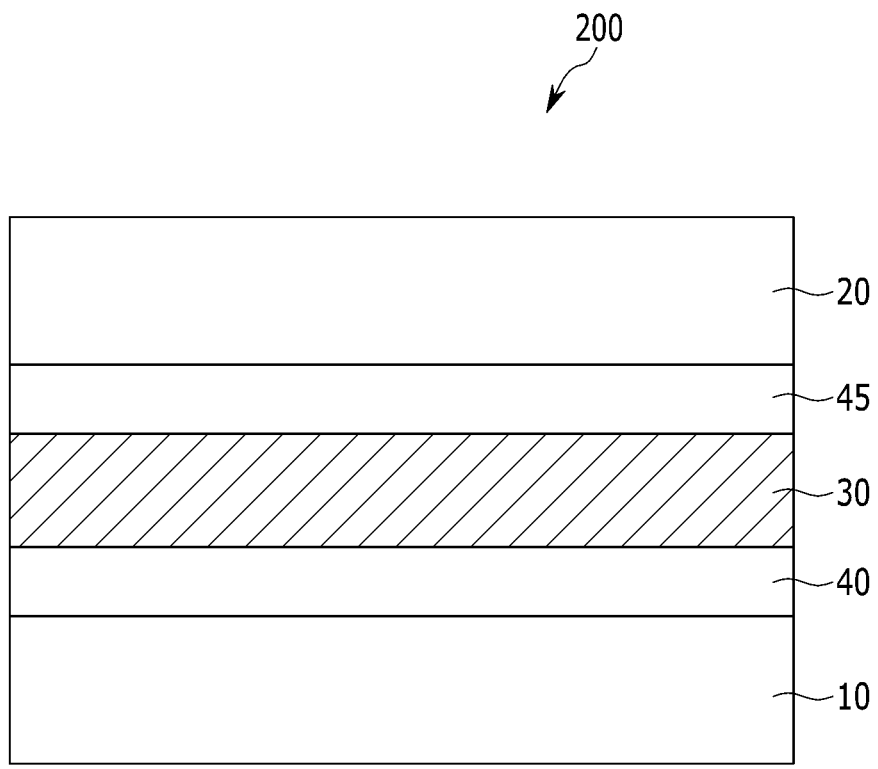
FIG. 2 is a cross-sectional view showing an organic photoelectric device according to another embodiment.

FIG. 2 is a cross-sectional view showing an organic photoelectric device according to another embodiment.

Referring to FIG. 2, an organic photoelectric device 200 according to the present embodiment includes a first electrode 10 and a second electrode 20 facing each other, and an active layer 30 between the first electrode 10 and the second electrode 20, like the above embodiment.

However, the organic photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include for example an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include for example one selected from poly(3,4-ethylenedioxythiophene):poly(styrenesulfonate) (PEDOT:PSS), polyarylamine, poly(N- vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron blocking layer (EBL) may include for example one selected from poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4''-tris(N-carbazolyl)-triphenylamine (TCTA), and a combination thereof, but is not limited thereto.

The electron transport layer (ETL) may include for example one selected from 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

The hole blocking layer (HBL) may include for example one selected from 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
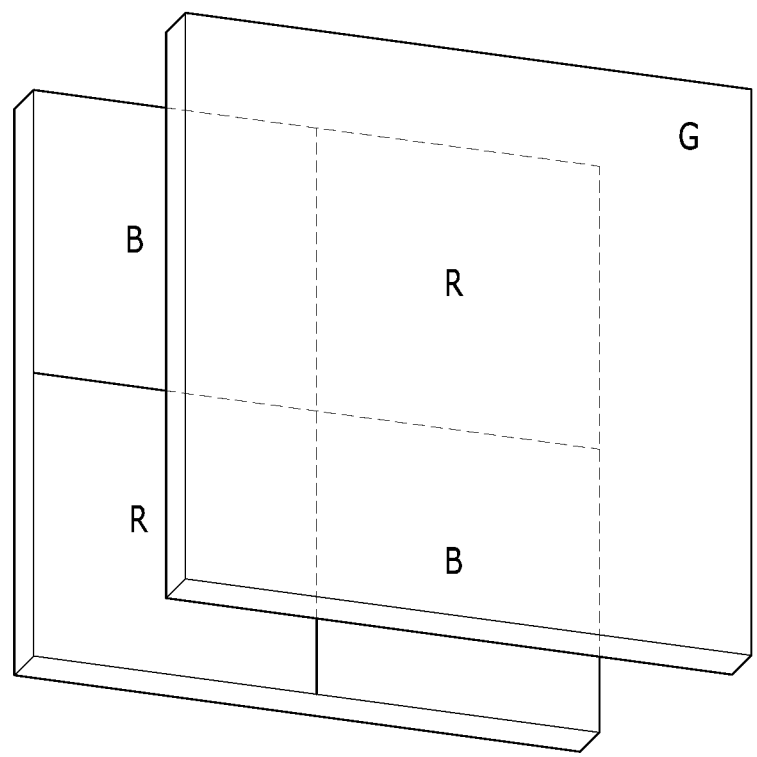
FIG. 3 is a schematic top plan view showing an organic CMOS image sensor according to an example embodiment.
Figure 4:
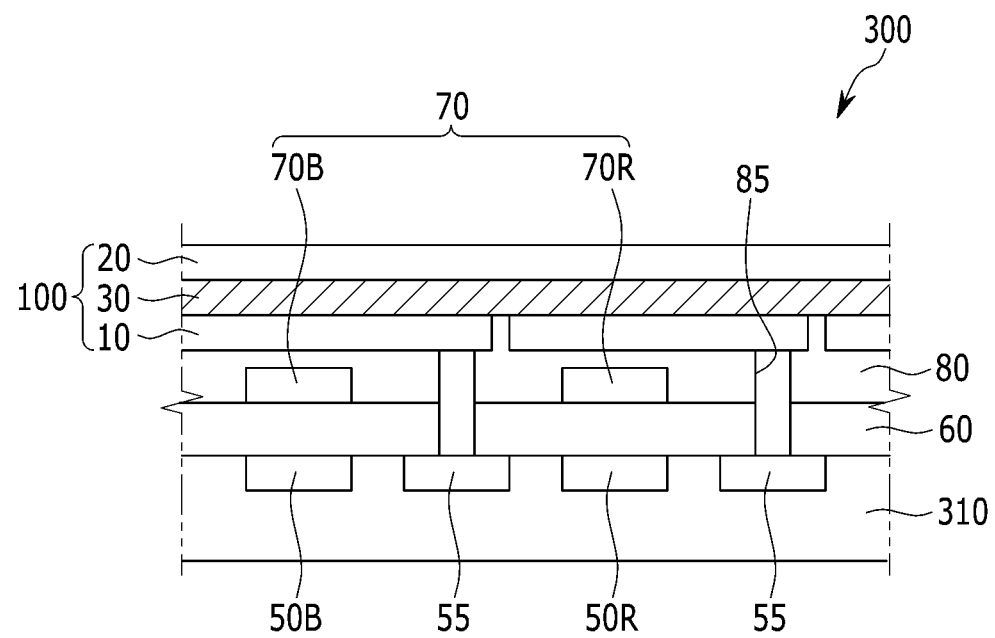
FIG. 4 is a cross-sectional view showing the organic CMOS image sensor of FIG. 3.

FIG. 3 is a schematic top plan view of an organic CMOS image sensor according to one embodiment, and FIG. 4 is a cross-sectional view of the organic CMOS image sensor of FIG. 3.

Referring to FIGS. 3 and 4, an organic CMOS image sensor 300 according to one embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and an organic photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected with the organic photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 310. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the organic photoelectric devices selectively absorbing and/or sensing light in a green wavelength region are stacked and thereby a size of an image sensor may be decreased and a down-sized image sensor may be realized.

As described above, the compound represented by the Chemical Formula 1 may be used as a p-type or n-type semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

Figure 5:
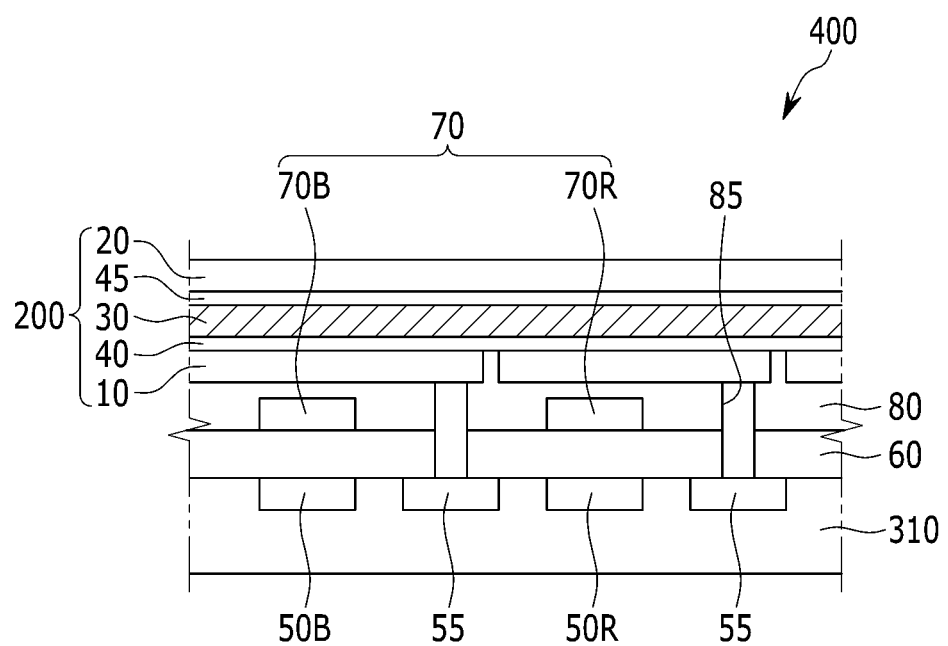
FIG. 5 is a schematic cross-sectional view showing an organic CMOS image sensor according to another example embodiment.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
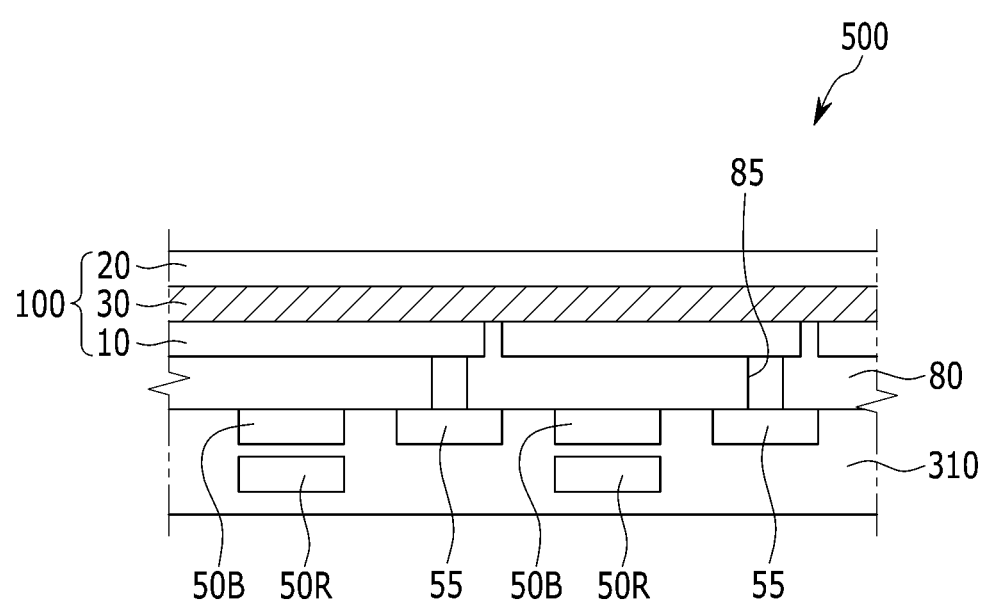
FIG. 6 is a schematic cross-sectional view showing an organic CMOS image sensor according to another example embodiment.

FIG. 6 is a cross-sectional view showing the organic CMOS image sensor according to another embodiment.

Referring to FIG. 6, the organic CMOS image sensor 500 includes a semiconductor substrate 310 integrated with photo-sensing devices 50B and 50R, a transmission transistor (not shown), a charge storage 55, an insulation layer 80, and an organic photoelectric device 100, like the example embodiment illustrated in FIG. 5.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the organic photoelectric devices selectively absorbing and/or sensing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
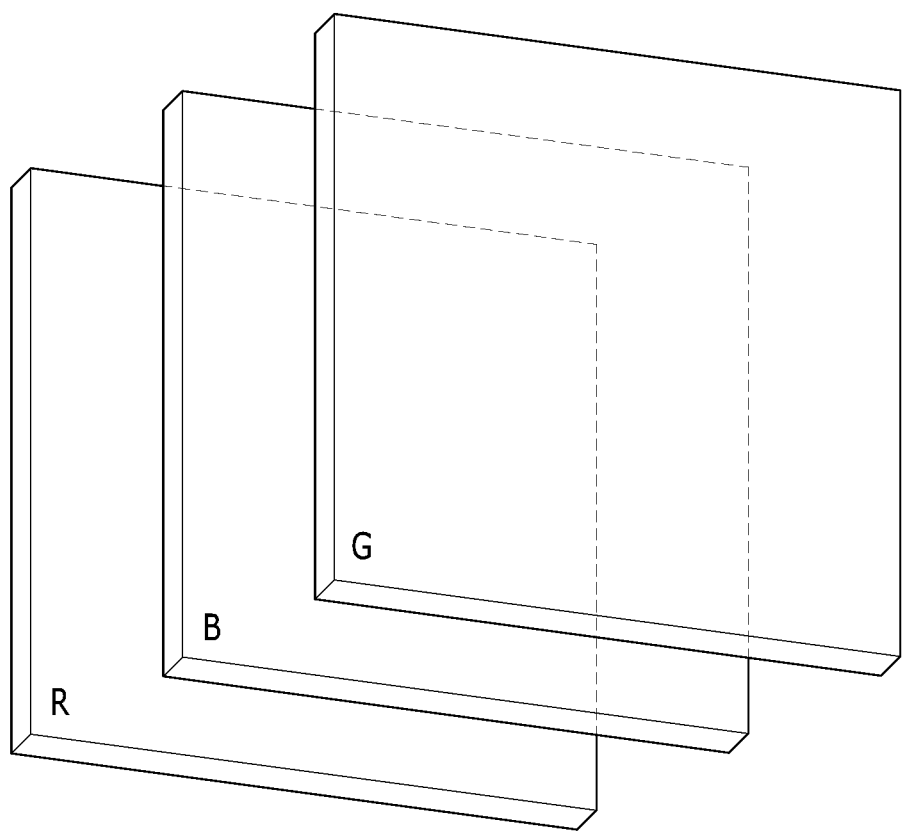
FIG. 7 is a schematic view showing an organic CMOS image sensor according to another example embodiment.

FIG. 7 is a schematic view showing an organic CMOS image sensor according to another embodiment.

Referring to FIG. 7, the organic CMOS image sensor according to the present embodiment includes a green photoelectric device (G) selectively absorbing and/or sensing light in a green wavelength region, a blue photoelectric device (B) selectively absorbing and/or sensing light in a blue wavelength region, and a red photoelectric device selectively absorbing and/or sensing light in a red wavelength region that are stacked.

In the drawing, the red photoelectric device (R), the green photoelectric device (B), and the blue photoelectric device (G) are sequentially stacked, but the stack order may be changed without limitation.

The green photoelectric device (G) may be the above organic photoelectric device 100, the blue photoelectric device (B) may include electrodes facing each other and an active layer interposed therebetween and including an organic material selectively absorbing light in a blue wavelength region, and the red photoelectric device (R) may include electrodes facing each other and an active layer interposed therebetween and including an organic material selectively absorbing light in a red wavelength region.

As described above, the organic photoelectric device (G) selectively absorbing and/or sensing light in a green wavelength region, the organic photoelectric device (R) selectively absorbing and/or sensing light in a red wavelength region, and the organic photoelectric device (B) selectively absorbing and/or sensing light in a blue wavelength region are stacked, and thereby a size of an image sensor may be decreased and a down-sized image sensor may be realized, and simultaneously sensitivity may be increased and a crosstalk may be decreased.

The image sensor may be applied to various electronic devices, for example, a mobile phone and/or a digital camera, but is not limited thereto.

Hereinafter, the present disclosure is illustrated in more detail with reference to examples. However, these are non-limiting examples, and the present disclosure is not limited thereto.

Synthesis Example 1: Synthesis of Compound Represented by Chemical Formula 1-1

[Chemical Formula 1-1]

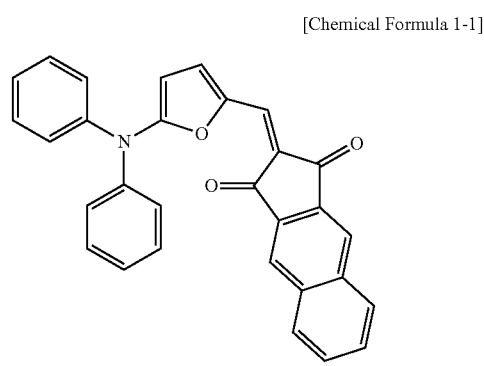 [SMILES: O=C1C(=Cc2ccc(N(c3ccccc3)c3ccccc3)o2)C(=O)c2cc3ccccc3cc21]

[Reaction Scheme 1-1]

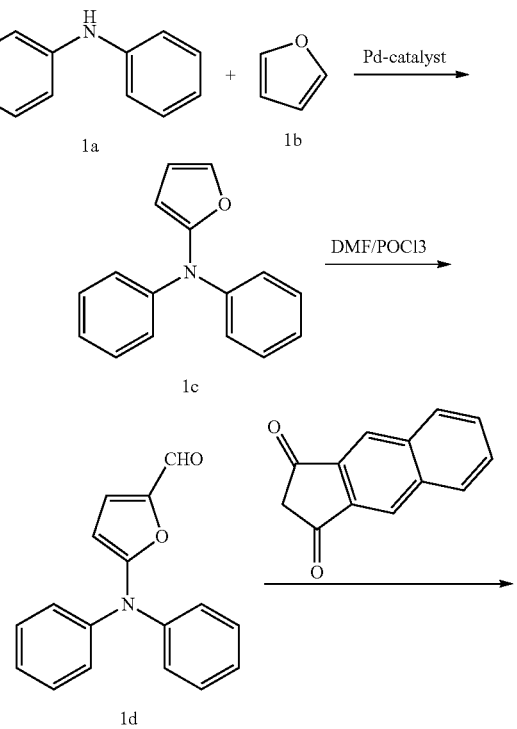

-continued

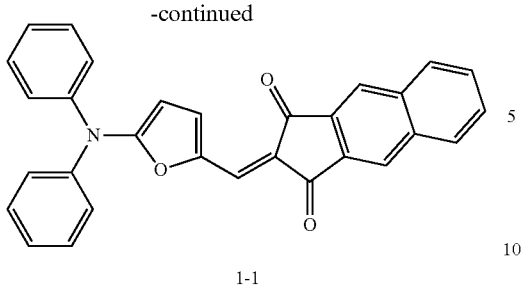

1-1

In Reaction Scheme 1-1, Compound 1c is synthesized according to Journal of Organic Chemistry, 68 7, 2861-2873; 2003. 2.35 g (10 mmol) of Compound 1c is dissolved in 20 ml of dichloro methane, dimethyl formamide (DMF, 0.80 g (11 mmol) is added thereto, and 3 ml of dichloro methane solution in which 1.69 g (11 mmol) of $POCl_3$ is dissolved is slowly dripped at 0° C. After dripping is completed, the resultant is stirred at room temperature (25° C.) for 1 hour and a NaOH aqueous solution is added to the reaction solution to complete a reaction. The resultant is extracted with dichloro methane, and 1.58 g (yield: 60%) of Compound 1d is produced by silica gel column chromatography.

Then, 1.32 g (5 mmol) of Compound 1d and 1.18 g (6 mmol) of benzoindandione are heated and stirred in 100 ml of ethanol (EtOH) at 60° C. for 3 hours. The produced crystal is recovered and recrystallized with dichloro methane/hexane to obtain 1.77 g (yield: 80%) of a compound represented by Chemical Formula 1-1.

$^1$H-NMR analysis result of compound represented by Chemical Formula 1-1 is as follows.

$^1$H NMR (ppm, $CDCl_3$); 9.19 (s, 1H), 8.28 (d, 2H), 8.02 (m, 2H), 7.59 (m, 3H), 7.45 (m, 4H), 7.35 (m, 6H), 5.87 (s, 1H).

Synthesis Example 2: Synthesis of Compound Represented by Chemical Formula 1-2

[Chemical Formula 1-2]

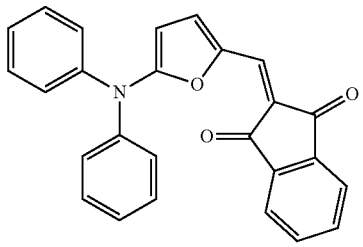

1,3-indandione is used instead of benzoindandione in Synthesis Example 1. 1.32 g (5 mmol) of Compound 1d of Synthesis Example 1 and 0.88 g (6 mmol) of 1,3-indandione are heated and stirred in 100 ml of EtOH at 60° C. for 3 hours. The produced crystal is recovered and recrystallized with dichloromethane/hexane to obtain 1.77 g (yield: 80%) of a compound represented by Chemical Formula 1-2.

$^1$H-NMR analysis result of compound represented by Chemical Formula 1-2 is as follows.

$^1$H NMR (ppm, $CDCl_3$); 9.17 (d, 1H), 8.10 (s, 1H), 7.91 (m, 2H), 7.71 (m, 2H), 7.47 (t, 4H), 7.38 (t, 2H), 7.31 (t, 4H), 5.91 (s, 1H)

Synthesis Example 3: Synthesis of Compound Represented by Chemical Formula 1-3

[Chemical Formula 1-3]

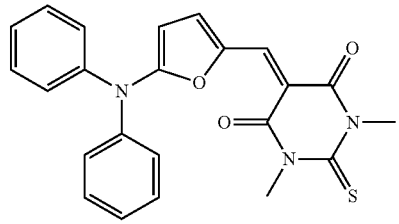

Dimethylthiobarbituric acid is used instead of benzoindandione in Synthesis Example 1. 1.32 g (5 mmol) of Compound 1d of Synthesis Example 1 and 0.86 g (6 mmol) of dimethylthiobarbituric acid are heated and stirred in 100 ml of EtOH at 60° C. for 3 hours. The produced crystal is recovered and recrystallized with dichloromethane/hexane to obtain 1.57 g (yield: 75%) of a compound represented by Chemical Formula 1-3.

$^1$H-NMR analysis result of compound represented by Chemical Formula 1-3 is as follows.

$^1$H NMR (ppm, $CDCl_3$); 9.17 (d, 1H), 8.10 (s, 1H), 7.47 (t, 4H), 7.38 (t, 2H), 7.31 (t, 4H), 5.91 (s, 1H), 3.79 (s, 6H)

Comparative Synthesis Example 1: Synthesis of Compound Represented by Chemical Formula 1-4

[Chemical Formula 1-4]

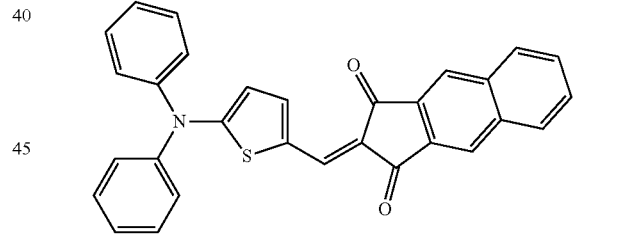

[Reaction Scheme 1-4]

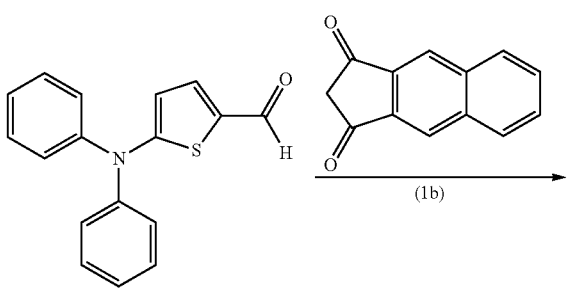

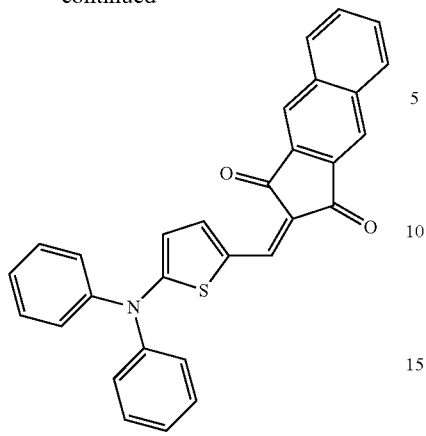

A compound represented by Chemical Formula 1-4 is synthesized according to Reaction Scheme 1-4. Compound 1a is synthesized according to Dalton Transactions, 44 3, 1473-1482; 2015. 10 mmol (2.8 g) of produced Compound 1a and 12 mmol (2.4 g) of Compound 1b are heated and refluxed in 100 ml of ethanol (EtOH) for 2 hours. Precipitated solids are collected and recrystallized with dichloromethane/hexane to obtain 4.1 g (yield: 90%) of a compound represented by Chemical Formula 1-4.

$^1$H NMR ppm (CDCl$_3$) 8.85 (s, 2H), 8.46 (s, 1H), 8.15 (m, 2H), 7.76 (m, 2H), 7.40 (d, 1H), 7.24 (m, 4H), 7.04 (m, 6H), 6.36 (d, 1H)

Comparative Synthesis Example 2: Synthesis of Compound Represented by Chemical Formula 1-5

[Chemical Formula 1-5]

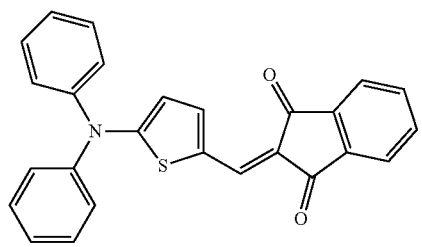

[Reaction Scheme 1-5]

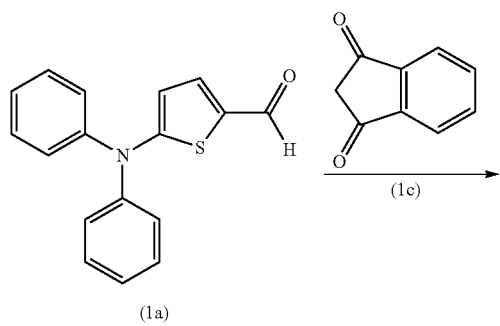

A compound (yield: 85%) represented by Chemical Formula 1-5 is obtained according to the same method as Comparative Synthesis Example 1 except for using Compound (1c) using Compound (1b) of Comparative Synthesis Example 1.

$^1$H NMR ppm (CDCl3) 8.46 (s, 1H), 7.93 (m, 2H), 7.71 (m, 2H), 7.40 (d, 1H), 7.24 (m, 4H), 7.04 (m, 6H), 6.36 (d, 1H)

Comparative Synthesis Example 3: Synthesis of Compound Represented by Chemical Formula 1-6

[Chemical Formula 1-6]

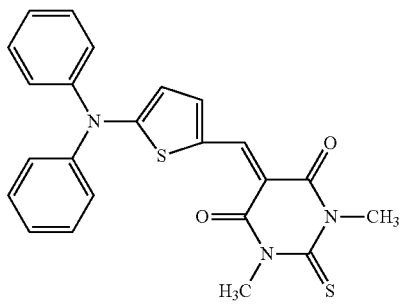

[Reactopm Scheme 1-6]

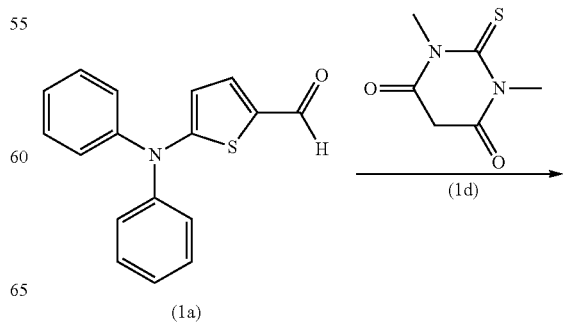

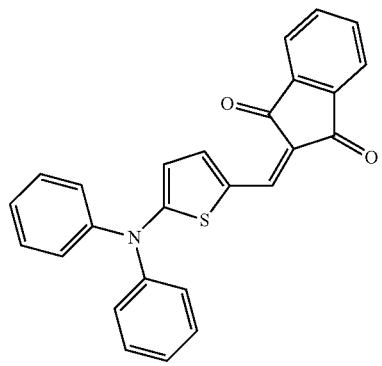

-continued

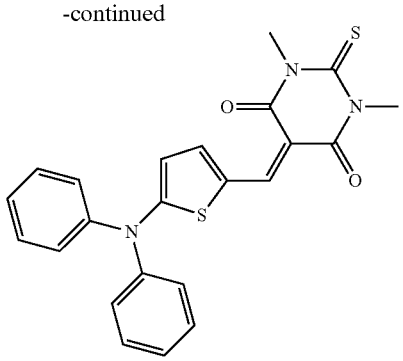

A compound (yield: 80%) represented by Chemical Formula 1-6 is obtained according to the same method as Comparative Synthesis Example 1 except for using Compound (1d) using Compound (1b) of Comparative Synthesis Example 1.

$^1$H HNMR ppm (CDCl3) 8.01 (s, 1H), 7.40 (d, 1H), 7.24 (m, 4H), 7.04 (m, 6H), 6.36 (d, 1H), 3.52 (s, 6H)

Light Absorption Characteristics of Compounds of Synthesis Examples 1 to 3 and Comparative Synthesis Examples 1 to 3

Light absorption characteristics depending on a wavelength of the compounds according to Synthesis Examples 1 to 3 and Comparative Synthesis Examples 1 to 3 are evaluated.

Compounds of Synthesis Examples 1 to 3 are thermally evaporated under high vacuum (<$10^{-7}$ Torr) at 0.5 to 1.0 A/s to respectively form a 70 nm-thick thin film, ultraviolet (UV)-visible rays (UV-Vis) are irradiated thereinto with Cary 5000 UV spectroscopy (Varian Inc.), and maximum absorption wavelengths, full widths at half maximum (FWHM) and energy levels are measured. Compounds of Synthesis Examples 1 to 3 are dissolved in toluene with $1.0 \times 10^{-5}$ mol/L respectively, ultraviolet (UV)-visible rays (UV-Vis) are irradiated thereinto with Cary 5000 UV spectroscopy (Varian Inc.), and molar absorption coefficients are measured. The results are shown in Table 1.

TABLE 1

| | $\lambda_{max}$ (nm) | FWHM (nm) | Energy level HOMO (eV) | LUMO (eV) | Molar absorption coefficient (cm$^{-1}$ M$^{-1}$)* |
|---|---|---|---|---|---|
| Synthesis Example 1 | 553 | 120 | −5.38 | −3.49 | 93755 |
| Synthesis Example 2 | 527 | 108 | −5.37 | −3.35 | 82715 |
| Synthesis Example 3 | 529 | 104 | −5.61 | −3.54 | 88853 |

Referring to Table 1, the compounds of Synthesis Examples 1 to 3 show a maximum absorption wavelength in a green wavelength region, a narrow full width at half maximum (FWHM), and high molar absorption coefficients. Accordingly, the compounds of Synthesis Examples 1 to 3 have improved green wavelength selectivity.

In addition, the compounds of Synthesis Examples 1 to 3 have a difference between HOMO and LUMO energy levels of about 2.0 eV or so in thin film state and thus, similar energy bandgaps to each other.

Example 1: Manufacture of Organic Photoelectric Device

An about 150 nm-thick anode is formed by sputtering ITO on a glass substrate, and a 85 nm-thick active layer is formed by codepositing the compound of Synthesis Example 1 (a p-type semiconductor compound) and C60 (an n-type semiconductor compound) in a thickness ratio of 1:1 thereon. Subsequently, a 30 nm-thick molybdenum oxide (MoO$_x$, 0<x≤3) thin film is laminated as a charge auxiliary layer thereon. Then, an 80 nm-thick cathode is formed by sputtering ITO on the molybdenum oxide thin film, manufacturing an organic photoelectric device.

Examples 2 to 4: Manufacture of Organic Photoelectric Device

Each organic photoelectric device according to Examples 2 to 4 is manufactured according to the same method as Example 1, except for using each compound according to Synthesis Examples 2 to 4, instead of the compound of the Synthesis Example 1.

Comparative Examples 1 to 3: Manufacture of Organic Photoelectric Device

Each organic photoelectric device according to Comparative Examples 1 to 3 is manufactured according to the same method as Example 1, except for using each compound according to Comparative Synthesis Example 1 to 3, instead of the compound of the Synthesis Example 1.

While some example embodiments have been described, it is to be understood that inventive concepts are not limited to the disclosed embodiments, but, on the contrary, are intended to cover various modifications and equivalent arrangements included within the spirit and scope of the appended claims.

<Description of symbols>

| | |
|---|---|
| 10: first electrode | 20: second electrode |
| 30: active layer | 40, 45: charge auxiliary layer |
| 100, 200: organic photoelectric device | 300, 400, 500: organic CMOS image sensor |
| 310: semiconductor substrate | 70B: blue filter 70R: red filter |
| 70: color filter layer | 85: through-hole |
| 60: lower insulation layer | 80: upper insulation layer |
| 50B, 50R: photo-sensing device | 55: charge storage |

What is claimed is:
1. A compound represented by Chemical Formula 1

[Chemical Formula 1]

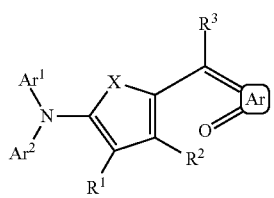

wherein, in Chemical Formula 1,
Ar is one of a substituted or unsubstituted 5-membered aromatic ring, a substituted or unsubstituted 6-membered aromatic ring, and a combination thereof in a condensed ring, X is one of O and NR$^a$ (wherein R$^a$ is one of hydrogen and a substituted or unsubstituted C1 to C10 alkyl group), each of Ar$^1$ and Ar$^2$ are independently one of a substituted or unsubstituted C6 to C30 aryl group and a substituted or unsubstituted C3 to C30 heteroaryl group, and each of R$^1$, R$^2$, and R$^3$ are independently one of hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, and a combination thereof.

2. The compound of claim 1, wherein at least one of Ar$^1$ and Ar$^2$ is independently one of a substituted or unsubstituted phenyl group, a substituted or unsubstituted naphthyl group, a substituted or unsubstituted anthracenyl group, a substituted or unsubstituted phenanthrenyl group, a substituted or unsubstituted pyridinyl group, a substituted or unsubstituted pyridazinyl group, a substituted or unsubstituted pyrimidinyl group, a substituted or unsubstituted pyrazinyl group, a substituted or unsubstituted quinolinyl group, a substituted or unsubstituted isoquinolinyl group, a substituted or unsubstituted naphthyridinyl group, a substituted or unsubstituted cinnolinyl group, a substituted or unsubstituted quinazolinyl group, a substituted or unsubstituted phthalazinyl group, a substituted or unsubstituted benzotriazinyl group, a substituted or unsubstituted pyridopyrazinyl group, a substituted or unsubstituted pyridopyrimidinyl group, and a substituted or unsubstituted pyridopyridazinyl group.

3. The compound of claim 1, wherein, in Chemical Formula 1, a ring group represented by Ar bound to a methine group is represented by Chemical Formula 2:

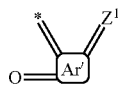

[Chemical Formula 2]

wherein, in Chemical Formula 2,

Ar' is one of a substituted or unsubstituted 5-membered aromatic ring, a substituted or unsubstituted 6-membered aromatic ring, and a combination thereof in a condensed ring, and Z$^1$ is one of O and CR$^b$R$^c$, wherein R$^b$ and R$^c$ are independently one of hydrogen, a substituted or unsubstituted C1 to C10 alkyl group, a cyano group, and a cyano-containing group, provided that at least one of R$^b$ and R$^c$ is a cyano group or a cyano-containing group.

4. The compound of claim 1, wherein, in Chemical Formula 1, a ring group represented by Ar bound to a methine group is represented by Chemical Formula 3-1:

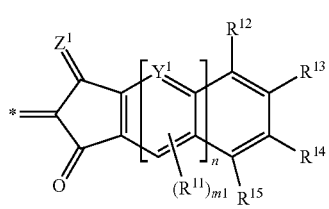

[Chemical Formula 3-1]

wherein, in Chemical Formula 3-1,

Z$^1$ is one of O and CR$^b$R$^c$ (wherein R$^b$ and R$^c$ are independently one of hydrogen, a substituted or unsubstituted C1 to C10 alkyl group, a cyano group, and a cyano-containing group, provided that at least one of R$^b$ and R$^c$ is a cyano group or a cyano-containing group), Y$^1$ is one of N and CR$^d$ (wherein R$^d$ is one of hydrogen and a substituted or unsubstituted C1 to C10 alkyl group), each of R$^1$, R$^{12}$, R$^{13}$, R$^{14}$, and R$^{15}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, or R$^{12}$ and R$^{13}$ and R$^{14}$ and R$^{15}$ are independently linked with each other to form an aromatic ring, m1 is 0 or 1, and n is 0 or 1.

5. The compound of claim 1, wherein, in Chemical Formula 1, a ring group represented by Ar bound to a methine group is represented by Chemical Formula 3-2:

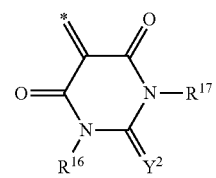

[Chemical Formula 3-2]

wherein, in Chemical Formula 3-2,

Y$^2$ is one of O, S, Se, Te, and C(R$^e$)(CN) (wherein R$^e$ is one of hydrogen, a cyano group (—CN), and a C1 to C10 alkyl group), and each of R$^{16}$ and R$^{17}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), and a combination thereof.

6. The compound of claim 1, wherein, in Chemical Formula 1, a ring group represented by Ar bound to a methine group is represented by Chemical Formula 3-3:

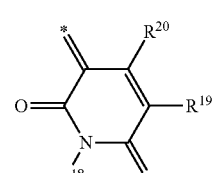

[Chemical Formula 3-3]

wherein, in Chemical Formula 3-3, each of R$^{18}$ to R$^{20}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof.

7. The compound of claim 1, wherein, in Chemical Formula 1, a ring group represented by Ar bound to a methine group is a ring group represented by Chemical Formula 3-4:

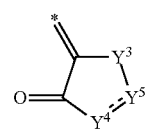

wherein, in Chemical Formula 3-4,

Y³ is one of O, S, Se, and Te,

Y⁴ is one of N and $NR^f$,

Y⁵ is one of $CR^g$ and $C=(CR^h)(CN)$, and each of $R^f$, $R^g$, and $R^h$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof.

8. The compound of claim 1, wherein the compound is represented by Chemical Formula 4-1:

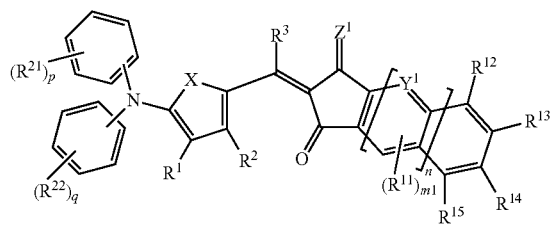

wherein, in Chemical Formula 4-1, $Z^1$ is one of O and $CR^bR^c$ (wherein each of $R^b$ and $R^c$ are independently one of hydrogen, a substituted or unsubstituted C1 to C10 alkyl group, a cyano group, and a cyano-containing group, provided that at least one of $R^b$ and $R^c$ is a cyano group or a cyano-containing group), $Y^1$ is one of N and $CR^d$ (wherein $R^d$ is one of hydrogen and a substituted or unsubstituted C1 to C10 alkyl group), each of $R^{11}$, $R^{12}$, $R^{13}$, $R^{14}$, and $R^{15}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof or $R^{12}$ and $R^{13}$ and $R^{14}$ and $R^{15}$ are independently linked with each other to form an aromatic ring, m1 is 0 or 1, n is 0 or 1, each of $R^{21}$ and $R^{22}$ are independently one of hydrogen, a halogen, a cyano group (—CN), a cyano-containing group, a substituted or unsubstituted C1 to C6 alkyl group, a substituted or unsubstituted C1 to C6 alkoxy group, and a combination thereof, p is an integer ranging from 0 to 3, and q is an integer ranging from 0 to 4.

9. The compound of claim 1, wherein the compound is represented by Chemical Formula 4-2:

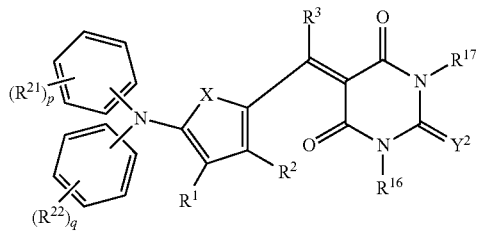

wherein, in Chemical Formula 4-2, $Y^2$ is one of O, S, Se, Te, and $C(R^e)(CN)$ (wherein $R^e$ is one of hydrogen, a cyano group (—CN), and a C1 to C10 alkyl group), each of $R^{16}$ and $R^{17}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, each of $R^{21}$ and $R^{22}$ are independently one of hydrogen, a halogen, a cyano group (—CN), a cyano-containing group, a substituted or unsubstituted C1 to C6 alkyl group, a substituted or unsubstituted C1 to C6 alkoxy group, and a combination thereof, p is an integer ranging from 0 to 3, and q is an integer ranging from 0 to 4.

10. The compound of claim 1, wherein the compound is represented by Chemical Formula 4-3:

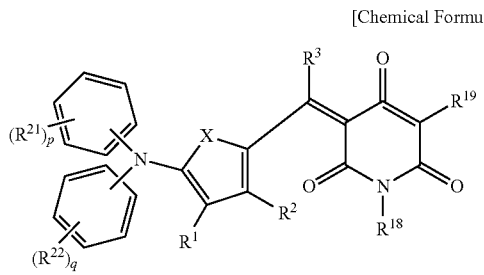

wherein, in Chemical Formula 4-3, each of $R^{18}$, $R^{19}$, and $R^{20}$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof, each of $R^{21}$ and $R^{22}$ are independently one of hydrogen, a halogen, a cyano group (—CN), a cyano-containing group, a substituted or unsubstituted C1 to C6 alkyl group, a substituted or unsubstituted C1 to C6 alkoxy group, and a combination thereof, p is an integer ranging from 0 to 3, and q is an integer ranging from 0 to 4.

11. The compound of claim 1, wherein the compound is represented by Chemical Formula 4-4:

[Chemical Formula 4-4]

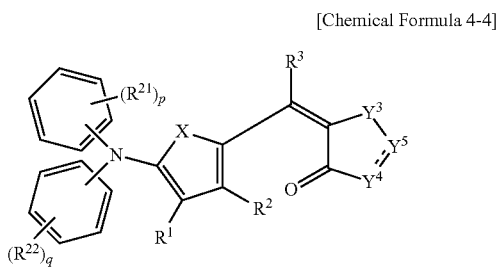

wherein, in Chemical Formula 4-4,
$Y^3$ is one of O, S, Se, and Te,
$Y^4$ is one of N and $NR^f$,
$Y^5$ is one of $CR^9$ and $C=(CR^h)(CN)$,
each of $R^f$, $R^g$, and $R^h$ are independently one of hydrogen, a substituted or unsubstituted C1 to C30 alkyl group, a substituted or unsubstituted C6 to C30 aryl group, a substituted or unsubstituted C4 to C30 heteroaryl group, a halogen, a cyano group (—CN), a cyano-containing group, and a combination thereof,
each of $R^{21}$ and $R^{22}$ are independently one of hydrogen, a halogen, a cyano group (—CN), a cyano-containing group, a substituted or unsubstituted C1 to C6 alkyl group, a substituted or unsubstituted C1 to C6 alkoxy group, and a combination thereof,
p is an integer ranging from 0 to 3, and
q is an integer ranging from 0 to 4.

12. The compound of claim 1, wherein the compound has a maximum absorption wavelength ($\lambda_{max}$) in a wavelength region of about 500 nm to about 600 nm in a thin film state.

13. The compound of claim 1, wherein the compound has a maximum absorption wavelength ($\lambda_{max}$) in a wavelength region of about 520 nm to about 560 nm in a thin film state.

14. The compound of claim 1, wherein the compound exhibits a light absorption curve having a full width at half maximum (FWHM) of about 50 nm to about 120 nm.

15. An organic photoelectric device, comprising:
a first electrode and a second electrode facing each other; and
an active layer between the first electrode and the second electrode
wherein the active layer includes the compound of claim 1.

16. The organic photoelectric device of claim 15, wherein the active layer has an absorption coefficient of greater than or equal to about $5.0 \times 10^4$ when including the compound and C60 in a volume ratio of about 0.9:1 to about 1.1:1.

17. An image sensor comprising the organic photoelectric device of claim 15.

18. The image sensor of claim 17, wherein the image sensor includes a semiconductor substrate integrated with a plurality of first photo-sensing devices sensing light in a blue wavelength region and a plurality of second photo-sensing devices sensing light in a red wavelength region, and
the organic photoelectric device on the semiconductor substrate and selectively sensing light in a green wavelength region.

19. The image sensor of claim 18, wherein the image sensor further includes a color filter layer between the semiconductor substrate and the organic photoelectric device, and including a blue filter selectively absorbing light in a blue wavelength region and a red filter selectively absorbing light in a red wavelength region.

20. The image sensor of claim 18, wherein the first photo-sensing device and the second photo-sensing device are stacked in a vertical direction in the semiconductor substrate.

21. The image sensor of claim 17, wherein the image sensor includes a green photoelectric device of the organic photoelectric device, a blue photoelectric device selectively absorbing light in a blue wavelength region, and a red photoelectric device selectively absorbing light in a red wavelength region that are stacked.

22. An electronic device comprising the image sensor of claim 17.

* * * * *